United States Patent [19]
Shin et al.

[11] Patent Number: 6,143,357
[45] Date of Patent: Nov. 7, 2000

[54] ALUMINUM COMPLEX DERIVATIVES FOR CHEMICAL VACUUM EVAPORATION AND THE METHOD OF PRODUCING THE SAME

[75] Inventors: Hyun-Koock Shin, Suwon; Hyun-Joo Shin, Seoul, both of Rep. of Korea

[73] Assignee: Rohm and Haas Company, Philadelphia, Pa.

[21] Appl. No.: 09/274,258

[22] Filed: Mar. 22, 1999

[30] Foreign Application Priority Data

Apr. 23, 1998 [KR] Rep. of Korea ....................... 98-14522

[51] Int. Cl.[7] ...................... C07D 207/00; C07D 333/46; C07F 5/06; B05D 5/12
[52] U.S. Cl. .................... 427/126.1; 544/225; 546/11; 548/402; 549/3; 549/206; 427/250
[58] Field of Search ................ 544/64, 225; 546/11; 548/402; 549/3, 206; 427/126.1, 250

[56] References Cited

U.S. PATENT DOCUMENTS

| | | | |
|---|---|---|---|
| 4,923,717 | 5/1990 | Gladfelter | 427/252 |
| 5,178,911 | 1/1993 | Gordon et al. | 427/255 |
| 5,180,687 | 1/1993 | Mikoshiba et al. | 437/187 |
| 5,191,099 | 3/1993 | Gladfelter et al. | 556/27 |
| 5,330,633 | 7/1994 | Matsumoto et al. | 204/298 |
| 5,393,699 | 2/1995 | Mikoshiba et al. | 437/187 |

OTHER PUBLICATIONS

Atwood et al., Inorg. Chem. vol. 32, No. 16, pp. 3482–3487, 1993.

"Reactions of Lithium Aluminum Hydride with Representative Elements of the Main Groups of the Periodic System" by Thomas Wartik and H. J. Schlesinger; J. Am. Chem. Soc. vol. 75 pp. 835–839, 1953.

*Primary Examiner*—Joseph McKane
*Assistant Examiner*—Taofiq A. Solola
*Attorney, Agent, or Firm*—S. Matthew Cairns

[57] ABSTRACT

Organometallic compounds useful for forming aluminum films by chemical vapor deposition are disclosed. Also disclosed are methods of preparing the organimetallic compounds and methods of forming aluminum films.

8 Claims, No Drawings

ALUMINUM COMPLEX DERIVATIVES FOR CHEMICAL VACUUM EVAPORATION AND THE METHOD OF PRODUCING THE SAME

BACKGROUND OF THE INVENTION

This invention relates generally to the field of chemical vapor deposition. In particular, this invention relates to the use of certain aluminum compounds for use in the chemical vapor deposition of aluminum films.

In the semiconductor industry, technological and material development have resulted in the miniaturization, high reliability, high speed, high functionality, and high degree of integration of devices, such as semiconductor integrated circuits. With the development of the manufacturing process of semiconductor devices, the development of improved memory devices, such as dynamic random access memory ("DRAM"), has been rapid. Currently, 64 mega DRAM is under mass production and, in the year 2,000, it is anticipated that with the new manufacturing methods of the next generation semiconductor devices, as well as with their mass production capabilities, 256 mega class memory devices may be available, as well as 1 giga ("G") and 4 G class high memory devices.

The next generation memory devices, those having high memory capacity, are the result of miniaturization of the memory device circuits; specifically, narrowing the line widths to 0.25, 0.18, and 0.15 microns ("$\mu$m").

The current wiring method in the semiconductor memory devices using aluminum as the wiring material is by vapor deposition, i.e., the sputtering method in which a metal, i.e., aluminum, itself is used for deposition to attain a desired thin film. This method limits the manufacturing process technology in achieving the narrowing of the line width described above.

In the manufacturing of 64 mega DRAM using aluminum (Al) metal wiring, the sputtering method has been the sole method used in the deposition of aluminum from an aluminum target. In the next generation memory devices described above, the circuit line width would be less than 0.25 $\mu$m and the aspect ratio (depth/diameter) of contact and via hole is large in the vapor deposited metal, thus, the use of sputtering in the vapor deposition process would be unsuitable.

To alleviate such a problem, an aluminum wiring process using chemical vapor deposition ("CVD") method has been studied for a long time. This method has a high step coverage and has an improved burying process of contact/via hole, which is an advantage of the method. Thus, aluminum wiring from vapor deposition of aluminum ("Al-CVD" or aluminum chemical vapor deposition) will be the foundation of the technology for the production of the next generation class memory devices and the CVD method is considered to be the imperative method.

In aluminum film deposition using the chemical vapor deposition method, an aluminum compound, known as the precursor, was used as the source material. The chemical properties and the selection of the compound greatly affect the CVD process and they are the most important elements in the process. Therefore, prior to the selection of the deposition method, it is imperative that the selection and development of the precursor are the first factors to be considered.

In spite of the importance of the role of a precursor, the metal film deposition process using CVD method has developed concurrently with the use of the process in the manufacture of the next generation semiconductor devices. For this reason the development of the precursors for Al-CVD has been delayed.

In the early stage of Al-CVD method development, alkyl aluminum compounds were widely used in the industry. The typical alkyl aluminum compounds commonly used were trimethylaluminum, as represented by the chemical formula of $Al(CH_3)_3$, and triisobutylaluminum, as represented by the chemical. formula of $[(CH_3)_2CHCH_3]Al$.

In the nineteen-nineties, the development of precursors for aluminum film deposition using the chemical vapor deposition process was very active in Japan resulting in the development of dimethylaluminum hydride, represented by the chemical formula of $[(CH_3)_2AlH]_2$, and in the USA resulting in the development of dimethylethylaminealane, represented by the chemical formula of $H_3AlN(CH_3)_2C_2H_5$. These compounds were leading precursors in the Al-CVD process.

Among the chemical compounds examined, dimethylethylaminealane was synthesized by Wayne Gladfelter of the University of Minnesota, in 1989, after the report of J. K. Ruff et al. in the Journal of the American Chemical Society, 1960. The synthesis of dimethylethylamine, $(N(CH_3)_2C_2H_5)$ has not been reported in the complex compound developed from aluminum hydride ($AlH_3$) and an alkyl amine in the report. U.S. Pat. No. 5,191,099 (Gladfelter et al.) discloses dimethylethylaminealane as a precursor in Al-CVD process.

Other chemicals, such as dimethylaluminum hydride, trimethylaluminum, and triisobutylaluminum, have been developed and have been used widely in various applications since the nineteen-fifties. Specifically, dimethylaluminum hydride was reported by T. Wartik et al., Journal of American Chemical Society, 1953, 75, 835, and trimethylaluminum and triisobutylaluminum have been reported quite a bit earlier than the above.

These compounds have been fully commercialized and used in many industrial areas prior to the nineteen-nineties. They can be obtained economically, and they are liquid at room temperature, which are their advantages. However, the above-mentioned compounds have some problems when used as the precursors in the Al-CVD process. The film deposition temperature is above 300° C. and near 400° C. Due to this high deposition temperature, the vapor deposition process becomes very difficult and the high temperature deposition results in the inclusion of carbon impurities which increase the electric resistance of the deposited film, which are the detrimental flaws.

To alleviate such problems in the Al-CVD process, a dimethylaluminum hydride precursor and related technologies were developed in the early part of the nineteen-eighties. Dimethylaluminum hydride has a high vapor pressure (2 torr at 25° C.) and its vapor deposition rate is high and it is a colorless liquid compound at room temperature. Also, advantageously, it provides very pure aluminum film deposition. However, dimethylaluminum hydride is an alkylaluminum compound that explodes when it comes into contact with air. Therefore, it is very difficult to handle and has high degree of difficulty in the manufacturing process which results in a low yield and high cost. Moreover, the vapor deposition temperature is 260–300° C., which is a comparatively high temperature, and results in the high possibility of the inclusion of impurities in the thin film, which is also a disadvantage.

As alternative precursors in the Al-CVD process, the alane ($AlH_3$) derivatives were used besides dimethylaluminum hydride. One of the alane derivatives, dimethylethylaminealane, forms a vapor deposition film of high purity at low temperature, 100–200° C., according to the reaction described in Equation 1. Dimethylethylaminealane is a colorless chemical compound at room temperature and has a relatively high vapor pressure (1.5 torr at 25° C.). In comparison with dimethylaluminum hydride, the flammability is somewhat less and it can be manufactured by a comparatively simple process at a low cost, which is advantageous.

Equation 1

However, dimethylethylaminealane is thermally unstable at room temperature as well as during the vapor deposition process, which is carried out at 30° C. Hence, during the storage the precursor gradually decomposes in the container. This difficulty in room temperature storage is a disadvantage. For this reason, development and reproducibility of the vapor chemical deposition process has been difficult in semiconductor device manufacturing processes.

SUMMARY OF THE INVENTION

It has now been found that certain aluminum compounds solve the problems of the known aluminum precursor compounds for Al-CVD applications.

The present invention provides an organometallic compound of the formula

 (I)

wherein L is one or more Lewis bases capable of providing an unshared electron pair to the aluminum and is selected from thiophene, thiopyran or an organic amine of formula II or III

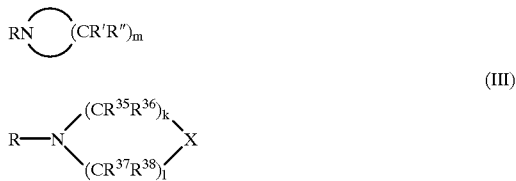

wherein R is an alkyl having a carbon number of 1 to 4; R', R", $R^{35}$, $R^{36}$, $R^{37}$ and $R^{38}$ are each independently hydrogen (H) or an alkyl group having carbon numbers of 1 to 2; X is oxygen or an alkyl group containing nitrogen; m is an integer from 2 to 8; k and l are each independently integers from 1 to 3; and n is 1 or 2.

The present invention also provides a vapor deposition precursor composition comprising an organometallic compound as described above.

The present invention also provides a process for aluminum film formation comprising the step of vapor depositing an aluminum film on a substrate, wherein the source of aluminum in the aluminum film is a vapor deposition precursor comprising an organometallic compound of the formula $H_3Al:L_n$; wherein L is one or more Lewis bases capable of providing an unshared electron pair to the aluminum and is selected from thiophene, thiopyran or an organic amine of formula II or III

wherein R is an alkyl having a carbon number of 1 to 4; R', R", $R^{35}$, $R^{36}$, $R^{37}$ and $R^{38}$ are each independently hydrogen (H) or an alkyl group having carbon numbers of 1 to 2; X is oxygen or an alkyl group containing nitrogen; m is an integer from 2 to 8; k and l are each independently integers from 1 to 3; and n is 1 or 2.

The present invention further provides a process for preparing an organometallic compound of the formula $H_3Al:L_n$; wherein L is one or more Lewis bases capable of providing an unshared electron pair to the aluminum and is selected from thiophene, thiopyran or an organic amine of formula II or III

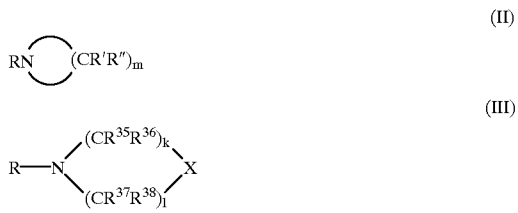

wherein R is an alkyl having a carbon number from 1 to 4; R', R", $R^{35}$, $R^{36}$, $R^{37}$ and $R^{38}$ are each independently hydrogen (H) or an alkyl group having carbon numbers of 1 to 2; X is oxygen or an alkyl group containing nitrogen; m is an integer from 2 to 8; k and l are each independently integers from 1 to 3; and n is 1 or 2, comprising the steps of: a) forming a suspension of aluminum chloride and lithium aluminum hydride in hexane or pentane; and b) adding to the suspension said Lewis base.

DETAILED DESCRIPTION OF THE INVENTION

This invention pertains to organometallic compounds useful as precursors in the vapor deposition of aluminum film as wiring on semiconductor devices and methods of preparing the precursor compounds.

Lewis bases capable of providing an unshared electron pair to the aluminum metal center are useful in the present invention Suitable Lewis bases include thiophene, thiopyran, and organic amine derivatives of Formula II or Formula III. For example, the organic amine derivatives include one or more heterocyclic amines selected from alkylaziridine, alkylazetidine, alkylpyrrolidine, alkylpiperidine, alkylhexamethyleneimine, alkylheptamethyleneimine, alkylmorpholine, 1,4-dialkylpiperazine.

In the above Formula II, R is an alkyl having a carbon number of 1 to 4, R' and R" are each independently hydrogen (H) or an alkyl group having carbon numbers of 1 to 2, and m is an integer of 2 to 8. In compounds of Formula II, it is preferred that R is methyl or ethyl.

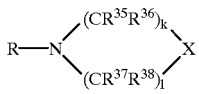
(III)

In the above Formula III, R is an alkyl group having carbon numbers of 1 to 4, $R^{35}$, $R^{36}$, $R^{37}$ and $R^{38}$ are each independently hydrogen (H) or alkyl group having a carbon number of 1 to 2, X is oxygen or an alkyl group containing nitrogen, and k and l are each independently integers of 1 to 3.

Among the compounds expressed by Formula II, the preferred compounds are alkylpyrrolidines having Formula IV and alkylpiperidines having Formula V. Among the compounds expressed by Formula III, the preferred compounds are alkylmorpholines having Formula VI and alkylpiperazines having Formula VII.

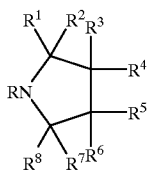
(IV)

In the above Formula IV, R is an alkyl group having a carbon number of 1 to 4, $R^1$ to $R^3$ are each independently hydrogen or alkyl group having a carbon number of 1 to 2. Preferred compounds of Formula IV are those wherein R is methyl or ethyl and $R^1$, $R^2$, $R^4$, $R^5$, $R^7$ and $R^8$ are each independently hydrogen or methyl.

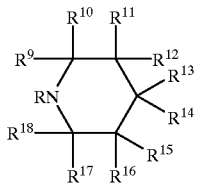
(V)

In the above Formula V, R is an alkyl group having a carbon number of 1 to 4, and $R^9$ to $R^{18}$ are each independently hydrogen or an alkyl group having a carbon number of 1 to 2. Preferred compounds of Formula V are those wherein R is methyl or ethyl and $R^9$, $R^{10}$, $R^{12}$, $R^{14}$, $R^{16}$, R17 and $R^{18}$ are each independently hydrogen or methyl.

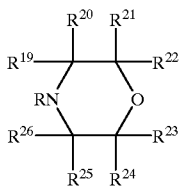
(VI)

In the above Formula VI, R is an alkyl group having a carbon number of 1 to 4, and $R^{19}$ to $R^{26}$ are each independently hydrogen or an alkyl group having a carbon number of 1 to 2. Preferred compounds of Formula VI are those wherein R is methyl or ethyl and $R^{19}$, $R^{20}$, $R^{21}$, $R^{22}$, $R^{23}$, $R^{24}$, $R^{25}$ and $R^{26}$ are each independently hydrogen or methyl.

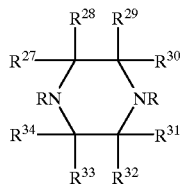
(VII)

In the above Formula VII, R is an alkyl group having a carbon number of 1 to 4, and $R^{27}$ to $R^{34}$ are each independently hydrogen or an alkyl group having a carbon number of 1 to 2. Preferred compounds of Formula VII are those wherein R is methyl or ethyl and $R^{27}$, $R^{28}$, $R^{29}$, $R^{30}$, $R^{31}$, $R^{32}$, $R^{33}$ and $R^{34}$ are each independently hydrogen or methyl.

In the above compounds having Formula II, suitable Lewis bases include: alkylpyrrolidines, such as 1-methylpyrrolidine having Formula VIII, 1-butylpyrrolidine having Formula IX and 1,4-dimethylpyrrolidine; alkylpiperidines, such as 1,2,2,6,6-pentamethylpiperidine, 1-methylpiperidine having Formula X and 1-ethylpiperidine having Formula XI; alkylmorpholines, such as 4-methylmorpholine having Formula XII and 4-ethylmorpholine having Formula XIII; and alkylpiperazines, such as 1,4-dimethylpiperazine having Formula XIV. These compounds are preferred for use as the precursors in the chemical vapor deposition of aluminum film. Especially preferred organic amines are 1-methylpyrrolidine, 1-methylpiperidine, 1-ethylpiperidine, 4-methylmorpholine, and 1,4-dimethylpiperazine.

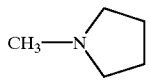
(VIII)

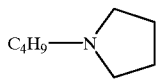
(IX)

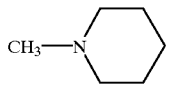
(X)

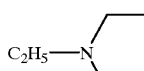
(XI)

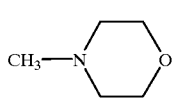
(XII)

(XIII)

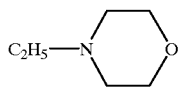

(XIV)

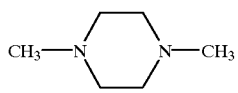

An aluminum compound represented by Formula I used for aluminum film vapor deposition can be readily prepared according to the chemical reaction represented by Equation 2. To a mixture of aluminum chloride powder and lithium aluminum hydride (LiAlH$_4$) in a reactor, hexane or pentane was added at room temperature to form a suspension and then a Lewis base, L, such as alkylpyrrolidine, alkylpiperidine, alkylmorpholine or alkylpiperazine, was added at room temperature to obtain the compounds of the present invention.

$$3LiAlH_4 + AlCl_3 + 10L \rightarrow 4H_3Al:L_n + 3LiCl \quad \text{Equation 2}$$

In the above Equation 2, L is a Lewis base as defined in Equation 1 and n is 1 or 2.

Among the Lewis base compounds, alkylpyrrolidine, such as 1-methylpyrrolidine, and alkylpiperidine, such as 1-methylpiperidine, are especially suitable. Therefore, the typical precursors for the chemical vapor deposition of aluminum film as wiring material in semiconductor devices are the compounds represented by Formula XV and Formula XVI, and the invention will be discussed in relation to these two compounds.

(XV)

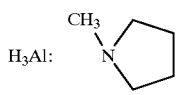

(XVI)

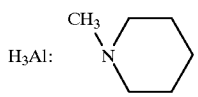

In the present invention, Formula XV and Formula XVI represent 1-methylpyrrolidinealane and 1-methylpiperidinealane, respectively, and their effects as precursors for aluminum film deposition are described below.

First, these compounds provide aluminum film deposition like dimethylethylaminealane, which is a well known precursor for aluminum film vapor deposition. The aluminum film was deposited according to the reaction path show below in a vapor deposition process and, thus, it is possible to form an aluminum film free of impurity inclusion at a low temperature, 100–200° C.

The reaction mechanism of 1-methylpyrrolidinealane in a vapor deposition process is shown in Equation 3.

Equation 3

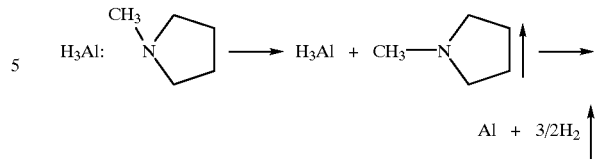

In the above Equation 3, the volatile reaction byproducts, such as 1-methylpyrrolidine and H$_2$, do not decompose at the vapor deposition temperature and the impurities are removed cleanly from the aluminum film and the silicon substrate. The reaction path of 1-methylpyrrolidinealane vapor deposition is the following: in the initial stage the gaseous precursor, 1-methylpyrrolidinealane, was fed into a reactor and was adsorbed as a gaseous phase onto the substrate surface, then the adsorbed 1-methylpyrrolidinealane on the substrate dissociates to 1-methylpyrrolidine, a gaseous Lewis base, which subsequently isolates as a gaseous byproduct. Then, the hydrogen in the remaining alane, the residue from the dissociation of 1-methylpyrrolidinealane, is removed and an aluminum film is formed on the substrate. In a chemical vapor deposition process, the compounds of the present invention may be vaporized by thermal energy, plasma or a bias applied on the substrate. It is preferred that the substrate be heated to 100° to 200° C. during the deposition process.

In the above Equation 3, in the dissociation stage of the 1-methylpyrrolidinealane adsorbed onto the substrate surface to 1-methylpyrrolidine gas, the rate determining factor is the formation of 1-methylpyrrolidine, a Lewis base. Hence, the dissociation to gas phase 1-methylpyrrolidine determines the rate of low temperature vapor deposition.

The aluminum film vapor deposition temperature of the known compounds, such as dimethylaluminum hydride, triisobutylaluminum hydride and trimethylaluminum, is 250° to 400° C., and the deposition temperature of one of the invention compounds, 1-methylpyrrolidinealane, is 100° to 200° C., and the invention compound provides a high vapor deposition rate of aluminum film at such a low temperature.

The low temperature vapor deposition technology of aluminum film is very important in semiconductor device manufacturing which requires multilayer metal wiring by metal vapor deposition, especially in the diffusion barrier during the upper layer metal vapor deposition process. As shown in Equation 3, the reaction path of 1-methylpyrrolidinealane produces 1-methylpyrrolidine and hydrogen (H$_2$) as the byproducts, and the hydrogen produced can be readily removed from the vapor deposition substrate as a gas. Also, 1-methylpyrrolidine does not decompose further in the vicinity of the vapor deposition temperature and can also be removed from the substrate as a gas. Therefore, a high purity aluminum film without impurity inclusions of either carbon or nitrogen can be obtained. The presence of impurities in the film will increase the electric resistance of the aluminum metal wiring, consequently, the signal transmission velocity will be retarded. Therefore, a high purity film is a very important factor in aluminum film vapor deposition.

The compounds of the present invention are similar to the known compound dimethylethylaminealane, which has been used for the precursor in aluminum film vapor deposition, but the invention compounds have improved thermal stability (decomposition during long-term storage) in comparison with the known compounds. For example, if 1-methylpyrrolidinealane in a bubbler was heated to 45° C.

to attain a sufficient vapor pressure for the vapor deposition (actual process temperature is 25–30° C.), characteristically, it does not decompose. These characteristics provide a reproducible aluminum film deposition process, which is extremely important in semiconductor device manufacturing, as well as provide long term storage stability at room temperature.

The conventional aluminum CVD precursor compounds, such as dimethylethylaminealane, trimethylaluminum and dimethylaluminum hydride, and the like, ignite explosively when in contact with water or air. The invention compounds are flammable but they do not ignite explosively or they are less flammable than the conventional precursors, so the risks of fire and personal injury are reduced. Additionally, the production cost, when compared with that of dimethylaluminum hydride, is very low. Thus, it is expected that the low cost and high quality aluminum film vapor deposition precursor will be obtained.

The invention compounds are a liquid at room temperature, and the control of the precursor compound delivery rate, which is closely related to process reproducibility, is easily achieved in the vapor deposition process by using a bubbler. Also, in other chemical vapor deposition processes that use a direct liquid injector or a liquid delivery system, the process can be carried out easily, which is an advantage.

Furthermore, as an added feature, the inventors developed precursor compound solutions which are more beneficial than known precursor solutions used in delivery systems such as direct liquid injectors and liquid delivery systems. A heterocyclic amine was used as the solvent for the preparation of a precursor solution for the delivery of the precursor compounds of Formula I, as the solute, in a delivery system. Examples of the heterocyclic amine solvent include 1-methylpyrrolidine, 1-butylpyrrolidine, 1-methylpiperidine, 1-ethylpiperidine, 4-methylmorpholine, 4-ethylmorpholine, 1,4-dimethylpiperazine, and the like. It is preferred that the solvent is 1-methylpyrrolidine. The solutes and the solvents are used in various combinations, and the resulting aluminum compound solutions can be used as effective precursors in aluminum vapor deposition processes.

In aluminum film vapor deposition, the invention solutions allow for the development of new processes when compared with that of conventional precursor solutions due to the wide selection of precursors.

Solutions of the above new compounds represented by Formula I were prepared using a heterocyclic amine as the solvent. The new precursor compound solution can be prepared by dissolving the invention compound represented by Formula I in a heterocyclic amine which is free of water, a purified solvent, and a Lewis base. The entire reaction is carried out under an inert gas atmosphere, such as a nitrogen or argon stream, to prevent the deterioration of the compound.

The invention compounds and the preparation of solutions of the compound will be discussed with examples.

EXAMPLE 1

Synthesis of 1-methylpyrrolidinealane 170 g (2.0 moles) of colorless 1-methylpyrrolidine was added dropwise at room temperature, while stirring, to a powder suspension consisting of 67 g (0.5 mole) of aluminum chloride and 65 g (1.7 moles) of lithium aluminum hydride in hexane under nitrogen stream. (The heat of reaction accompanied by the reaction is minute and it is not necessary to cool the reactor and the heat may aid in the reaction). After the addition of the 1-methylpyrrolidine, the reaction mixture was stirred for about 5 hours to complete the reaction, by the end of that period, the reaction product, 3-methylpyrrolidinealane began to coagulate gradually with the reactants and then settled. In the settled layer, an oily layer of 1-methylpyrrolidinealane was formed.

After the completion of the reaction, the invention compound, 1-methylpyrrolidinealane was separated from the reaction mixture by filtration in nitrogen stream to obtain a first filtrate. The byproducts on the filter were rinsed twice with a sufficient quantity of hexane, and then the rinsing solutions were added to the first filtrate. All of the volatile components in the filtrate were removed under vacuum to obtain a colorless liquid.

The dried colorless filtrate was distilled at 45° C. under vacuum ($10^{-2}$ torr) so as to condense the distillate in an ice chilled receiver. The colorless first filtrate was distilled in a similar manner at 40° C. to obtain 180 g of high purity 1-methylpyrrolidinealane.

The reaction shown in Equation 4 is the preparation of 1-methylpyrrolidinealane, and the highly purified 1-methylpyrrolidinealane was analyzed by proton nuclear magnetic resonance ("NMR") and the data and properties are listed in Table 1.

Equation 4

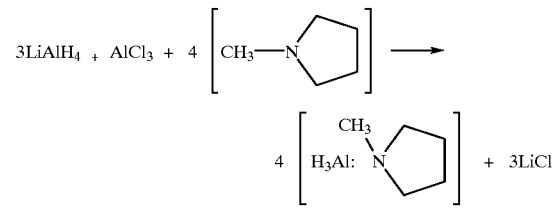

EXAMPLE 2

Synthesis of 1-methylpiperidinealane

To a suspension of aluminum chloride and lithium aluminum hydride in hexane prepared according to Example 1, 198 g (2.0 moles) of 1-methylpiperidine were added dropwise at room temperature in a nitrogen stream and the mixture was then stirred for 5 hours. Similar to Example 1, the suspension coagulated and 1-methylpiperidinealane settled on the bottom of the reactor showing a liquid phase separation. A colorless liquid was obtained following the procedure of Example 1. The hexane solvent was removed under vacuum ($10^{-2}$ torr) at 20° C. This partially dried solution was stored in a freezer at –20° C. overnight to crystallize 1-methylpiperidinealane from its liquid state. To collect the compound, 1-methylpiparidinealane, the supernatant, which resulted from the crystallization at –20° C., was separated and the compound was dried under vacuum to obtain 210 g of colorless liquid.

The dried colorless liquid compound was distilled at 45° C. under vacuum ($10^{-3}$ torr) and collected in a receiver chilled with dry ice (–78° C.) to obtain 155 g of high purity distillate of 1-methylpiperidinealane.

The reaction shown in Equation 5 is the preparation of 1-methylpiperidinealane, and the synthesized compound was analyzed by proton nuclear magnetic resonance and the data and the observed properties are listed in Table 1. The results confirmed the compound as 1-methylpippridinealane.

Equation 5

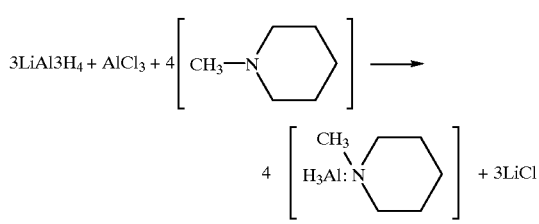

EXAMPLE 3

Synthesis of 1-ethylpiperidinealane

To a suspension of aluminum chloride and lithium aluminum hydride in hexane prepared according to Example 1, 226 g (2.0 moles) of 1-ethylpiperidine were added dropwise at room temperature under a nitrogen atmosphere following the procedure of Example 1. According to the Example 2 procedure, the partially dried filtered solution was stored in a freezer at $-20°$ C. to precipitate crystals and then distilled to obtain 118 g of high purity 1-ethylpiperidinealane.

The reaction shown in Equation 6 is the preparation of 1-ethylpiperidinealane, and the product compound was analyzed by proton nuclear magnetic resonance. The data and the observed properties are listed in Table 1 and the product was confirmed as 1-ethylpiperidinealane.

Equation 6

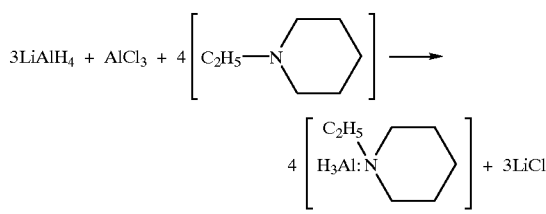

EXAMPLE 4

Synthesis of 4-methylmorpholinealane

To a suspension of aluminum chloride and lithium aluminum hydride in hexane prepared according to Example 1, 202 g (2 moles) of 4-methylmorpholine were added dropwise at room temperature under a nitrogen atmosphere according to the procedure of Example 1. After the completion of the reaction, the product was obtained by the same manner as in Example 1 and was separated to obtain 4-methylmorpholinealane.

The reaction shown in Equation 7 is the preparation of 4-, and the product compound was analyzed by proton nuclear magnetic resonance. The data and the observed properties are listed in Table 1 and the product was confirmed as 4-methylmorpholinealane.

Equation 7

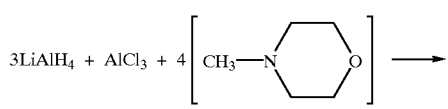

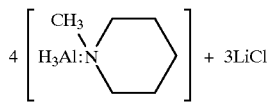

EXAMPLE 5

Synthesis of 1 4-dimethylpiperazinealane

To a suspension of aluminum chloride and lithium aluminum hydride in hexane prepared according to Example 1, 228 g (2 moles) of 1,4-dimethylpiperazine were added dropwise at room temperature under a notrogen atmosphere according to the procedure of Example 1. After the completion of the reaction, the product was obtained by the same manner as in Example 1 and was separated to obtain 1,4-dimethylpiperazinealane.

The reaction shown in Equation 8 is the preparation of 1,4-dimethylpiperazinealane, and the product compound was analyzed by proton nuclear magnetic resonance. The data and the observed properties are listed in Table 1 and the product was confirmed as 1,4-dimethylpiperazinealane.

Equation 8

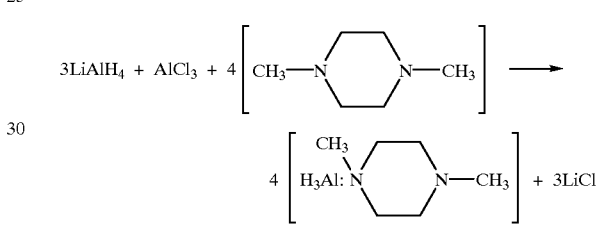

TABLE 1

| Example | Compound | Phase (20° C.) | Color | NMR Analysis ($C_6D_6$, ppm) |
|---|---|---|---|---|
| 1 | 1-Methylpyrrolidinealane | liquid | colorless | $\delta$ 1.40 (m, 4H) $\delta$ 2.04 (s, 3H) $\delta$ 2.41 (s, br, 4H) $\delta$ 4.09 (br, 3H) |
| 2 | 1-Methylpiperidinealane | liquid | colorless | $\delta$ 1.04 (p, 2H) $\delta$ 1.39 (m, br, 4H) $\delta$ 2.07 (s, 3H) $\delta$ 2.32 (m, br, 4H) $\delta$ 4.02 (br, 3H) |
| 3 | 1-Ethylpiperidinealane | liquid | colorless | $\delta$ 0.99 (t, 3H) $\delta$ 1.16 (m, 4H) $\delta$ 1.42 (m, 4H) $\delta$ 2.32 (m, 6H) $\delta$ 4.12 (br, 3H) |
| 4 | 4-Methylmorpholinealane | liquid | colorless | $\delta$ 0.87 (t, 3H) $\delta$ 2.15 (m, 4H) $\delta$ 3.59 (m, 4H) $\delta$ 4.21 (br, 3H) |
| 5 | 1,4-Dimethylpiperazinealane | liquid | colorless | $\delta$ 2.12 (s, 6H) $\delta$ 2.50 (br, 4H) $\delta$ 4.09 (br, 3H) |

EXAMPLE 6

Solution of 1-methylpyrrolidinealane 20 g of purified 1-methylpyrrolidine were added to 80 g of 1-methylpyrrolidinealane obtained by the procedure of Example 1 to obtain the invention colorless solution.

EXAMPLE 7

The compounds of the invention, 1-methylpyrrolidinealane prepared in Example 1,1-methylpiperidinealane prepared in Example 2, and the 1-methylpyrrolidine solution of 1-methylpyrrolidinealane prepared in Example 6, were tested for aluminum vapor deposition.

Test 1

The compounds synthesized in Example 1 and Example 2, 1-methylpyrrolidinealane and 1-methylpiperidinealane, respectively, were each added to a stainless steel bubbler. Argon or nitrogen gas was bubbled through the solution at a flow rate of 100–600 SCCM (standard cubic centimeters per minute or cm³/minute) while maintaining the bubbler at 30–40° C.

The vaporized precursor compound was diluted by the carrier gas and passed through a stainless steel tube at 40–50° C. into a reactor containing a substrate for film vapor deposition. The walls of the reactor were heated to 40–50° C. to prevent the condensation of the precursor. The substrate, 2,000 Angstrom thick SiO$_2$ coated with a 900 Angstrom thick TiN layer and heated at 100–200° C., was coated with a high purity aluminum film by vapor deposition process. The vapor deposited aluminum film was measured for the impurity content by Auger electron spectroscopy and it was confirmed that the vapor deposited aluminum film is a high purity film. The sheet resistance was measured by a 4-point probe. The vapor deposition conditions and the analytical data are listed in Table 2.

TABLE 2

| Precursor | 1-Methylpyrrolidinealane | 1-Methylpipendinealane |
|---|---|---|
| Deposition Condition | | |
| Carrier Gas | Nitrogen | Argon |
| Bubbler Temperature (° C.) | 30–40 | 30–40 |
| Reactor Temperature (° C.) | 40–50 | 40–50 |
| Substrate Temperature (° C.) | 100–200 | 100–200 |
| Flow rate (SCCM) | 100–600 | 100–600 |
| Reactor Pressure (torr) | 0.1–6 | 0.1–6 |
| Thin Film | | |
| Deposition Rate (Å/min) | 1500–7000 | 1300–6000 |
| Resistivity (μ ohm-cm) | 2.8–3.5 | 2.8–3.5 |
| Impurity | None (by AES) | None (by AES) |
| Adhesion | Excellent on Titanium nitride | Excellent on Titanium nitride |
| Surface Reflectivity | Good | Good |

Test 2

The precursor compound solution prepared according to Example 6 was used to form an aluminum film by chemical vapor deposition method. The silicon substrate was the same as the one used in Test 1 and the substrate temperature was 100–200° C. The reactor vessel, a glass tube having 5 cm inside diameter and 30 cm length, had one closed end and the open end was connected to a vacuum pump (10$^{-2}$ torr). The precursor solution was filled in a 2 milliliter ("mL") glass container and the glass container was placed in the closed end of the reactor. Several thin silicon pieces were placed in the reactor. The precursor solution and the substrate were maintained at 40° C. and 100–200° C., respectively, using independent heating wire and, while heating the solution and the substrates, the reactor was evacuated by vacuum pump to 10$^{-2}$ torr to obtain a vapor deposited high purity aluminum film. The vapor deposited film was tested by Auger electron spectroscopy ("AES") and a 4-point probe test. The results, which confirmed that the aluminum film is high purity, are listed in Table 3. This further shows that the invention solution is suitable for direct liquid injector and liquid delivery system as the liquid precursor delivery system.

TABLE 3

| Precursor: | 1-Methylpyrrolidinealane dissolved in 1-Methylpyrrolidine |
|---|---|
| Deposition Condition | |
| Evaporation Temperature (° C.) | 45 |
| Substrate Temperature (° C.) | 100–200 |
| Reactor Pressure (torr) | 0.1–1 |
| Thin Film | |
| Resistivity (μ ohm-cm) | 2.5–3.2 |
| Impurity | None (by AES) |
| Adhesion | Excellent on Titanium nitride |
| Deposition Rate (Å/min) | 1700–5000 |

As discussed in Example 1 and Example 2, the invention compounds can be vapor deposited to form thin films at a low substrate temperature, namely 100–200° C. Also, the deposition rate of the aluminum film on a silicon substrate, resistance, impurity, adhesion strength, and reflectance are superior to the use of known precursors. Moreover, the invention precursor can be used in direct liquid injector or liquid delivery system in the vapor deposition process, which is an advantage.

What is claimed:

1. An organometallic compound of the formula

wherein L is one or more Lewis bases capable of providing an unshared electron pair to the aluminum and is selected from thiophene, thiopyran or an organic amine of formula II or VII

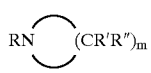

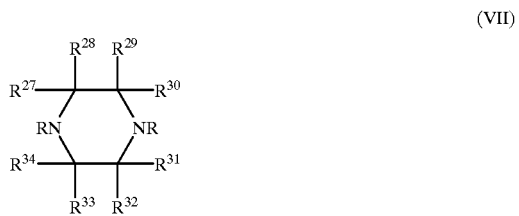

wherein
   R is an alkyl having a carbon number of 1 to 4;
   R', R", R$^{27}$, R$^{28}$, R$^{29}$, R$^{30}$, R$^{31}$, R$^{32}$, R$^{33}$ and R$^{34}$ are each independently hydrogen or an alkyl group having carbon numbers of 1 to 2;
   m is an integer from 2 to 8; and
   n is 1 or 2.

2. The compound of claim 1, wherein the organic amine is one or more selected from alkylaziridine, alkylazetidine, alkylpyrrolidine, alkylpiperidine, alkylhexamethyleneimine, alkylheptamethyleneimine, or alkyipiperazine.

3. The compound of claim 2, wherein the organic amine is one or more selected from 1-methylpyrrolidine, 1-butylpyrrolidine, 1,4-dimethylpyrrolidine, 1-methylpiperidine, 1-ethylpiperidine, 1,2,2,6,6-pentamethylpiperidine, or 1,4-dimethylpiperazine.

4. The compound of claim 1 wherein the Lewis base is selected from thiophene or thiopyran.

5. A vapor deposition precursor composition comprising an organometallic compound of claim 1 and a heterocyclic amine solvent.

6. The composition of claim 5, wherein the heterocyclic amine solvent is one or more selected from 1-methylpyrrolidine, 1-butylpyrrolidine, 1-methylpiperidine, 1-ethylpiperidine, 4-methylmorpholine, 4-ethylmorpholine, or 1,4-dimethylpiperazine.

7. A process for preparing an organometallic compound of the formula $H_3Al:L_n$; wherein L is one or more Lewis bases capable of providing an unshared electron pair to the aluminum and is selected from thiophene, thiopyran or an organic amine of formula II or VII,

(II)

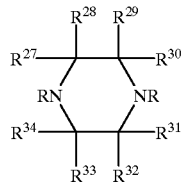
(VII)

wherein

R is an alkyl having a carbon number of 1 to 4;

R', R", $R^{27}$, $R^{28}$, $R^{29}$, $R^{30}$, $R^{31}$, $R^{32}$, $R^{33}$ and $R^{34}$ are each independently hydrogen or an alkyl group having carbon numbers of 1 to 2;

m is an integer from 2 to 8; and n is 1 or 2, comprising the steps of: a) forming a suspension of aluminum chloride and lithium aluminum hydride in hexane or pentane; and b) adding to the suspension said Lewis base.

8. The process of claim 7, wherein the organic amine is one or more selected from 1-methylpyrrolidine, 1-butylpyrrolidine, 1,4-dimethylpyrrolidine, 1-methylpiperidine, 1-ethylpiperidine, 1,2,2,6,6-pentamethylpiperidine, or 1,4-dimethylpiperazine.

* * * * *